United States Patent [19]

Klemm

[11] Patent Number: Plant 7,149

[45] Date of Patent: Feb. 13, 1990

[54] GERANIUM PLANT NAMED MARPANET

[76] Inventor: Siegfried Klemm, Hanfacker 8, D-7000 Stuttgart 50, Fed. Rep. of Germany

[21] Appl. No.: 262,332

[22] Filed: Sep. 12, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinctive geranium plant characterized by its relatively large, well filled, ball-formed flower clusters on 14 cm. stalks and containing about seventy florets having the red purple color of the well known 'Kardinal'. Each floret has about six petals of uniform coloration and is well filled with a diameter of about 5 cm. providing clusters that stand predominantly above the dark green foliage which has good zonation. The plant is a bushy and compact variety with heavy branches of medium height with a vigorous and spreading growth habit and abundant foliage, with many leaves of medium size, which stands about 18 cm. above the soil.

1 Drawing Sheet

BACKGROUND OF THE NEW PLANT

This new plant originated as a seedling of the geranium variety 'PAC-614' (unpatented) as the seed parent growing at my nursery at Stuttgart, West Germany, and being random pollinated, was grown with the object of seed collection. This new plant was selected from among seedlings of the said hybrid parent because of its brilliant and unusual coloration and propagation of this selected plant was done by me and under my direction by means of cuttings at Stuttgart, West Germany, in 1985, with very satisfactory results, and such propagation of the new plant has been carried on through several successive generations, which demonstrated conclusively that the novel characteristics of the selected plant and its general homogeneity would hold true from generation to generation and appeared to be firmly fixed.

DESCRIPTION OF THE DRAWING

My new geranium cultivar is illustrated by the accompanying photographic drawing which, in full color, shows a flower and some foliage, the colors shown being as closely true to those herein specified as is reasonably possible to obtain by conventional, professional photographic procedures.

DESCRIPTION OF THE NEW PLANT

The following is a detailed description of my geranium cultivar with color designations according to the R.H.S. Colour Chart of The Royal Horticultural Society at London, England.

THE PLANT

Origin: Seedling.

Parentage:

*Seed parent.*—Geranium variety 'PAC-614' (unpatented).

*Pollen parent.*—Unknown.

Classification:

*Botanic.*—*Pelargonium zonale* Hybrid.

*Commercial.*—Geranium.

Form: Spreading bush of medium height with heavy branching.

Growth habit: Vigorous and spreading with good strength and a medium growth rate.

Foliage:

*Quantity.*—Abundant with many leaves.

*Leaf size.*—About 8.5 cm. wide and about 9.5 cm. long.

*Leaf shape.*—Reniform with bicrenate margins.

*Texture.*—Smooth.

*Ribs and veins.*—Seven or eight main veins on each leaf.

*Texture.*—Smooth.

*Color.*—Upper side — Medium green with favorable zonation. Under side — Lighter green and slightly hairy.

THE BUD

Size: Medium.

*Diameter.*—About 11 to 14 mm.

*Length.*—About 15 to 17 mm.

Shape: Generally elliptic with ovoid body and pointed tip.

Rate of opening: Medium.

Color of petals: When sepals first divide, white to light purple. When petals begin to unfurl, red/purple.

Sepals:

*Number.*—Five.

*Shape.*—Lanceolate.

*Character.*—The sepals stand up when flowers open.

*Color.*—Inside and outside — Green.

Calyx:

*Shape.*—Flat; almost no calyx.

*Size.*—Broad.

*Splitting.*—The calyx does not split.

*Aspect.*—Smooth to hairy.

THE INFLORESCENCE

Blooming habit: Continuous and profusely from early Spring to late Fall.

Florets:

*Size.*—Medium. Diameter — About 5 cm. Depth of the calyx — About 1 cm.

Borne: Singly on a stem of an umbel-formed cluster.

Shape: When bloom first opens, cup-shaped. When bloom matures, a flat cup.

Petalage:

*Number of petals.*—Six.

*Arrangement.*—Imbricated around the ovaries. Reniform with crenate margins.

*Texture.*—Soft.

*Appearance.*—Satiny-velvety.

*Color.*—Upper surface: Red/Purple, R.H.S. 66-A, with a shining area at the base of each petal.

Cluster stalk:

*Length.*—About 14 cm.

*Color.*—Green.

*Character.*—Upright and rigid.

Floret persistence: About six days; when the floret is old, the petals fall down cleanly.

Disease resistance: This plant is resistant to Botrytis as observed in the Stuttgart area during the summer of 1987.

Lasting quality of the cluster: On the plant, about fourteen days.

REPRODUCTIVE ORGANS

Stamens:

*Number.*—Seven.

*Arrangement.*—Encircling the ovaries and pistil.

Anthers.—Size: About 1.5 cm. Color: Light brown.

*Filaments.*—Length: About 3 to 4 mm. Color: Light green.

Pollen.—Color: Orange.

Pistil:

*Number.*—One.

*Style.*—Length: About 4 mm. Color: Light green to purple.

*Stigma.*—Color: Light purple, like Glass.

Character of ovaries: Normal.

THE FRUIT

Fertility: The fruit is fertile.

Shape: Ovoid.

Color at maturity: Brown.

This attractive new variety has the red-purple color of the flower of the popular 'Kardinal' variety but the growth rate is much better because it is a bushy and compact plant and does not grow so high and leggy. The leaves are dark green with favorable zonation and the blooming plant has a harmonious, compact appearance and does not get Botrytis in wet years.

I claim:

1. The new and distinct geranium variety, substantially as herein shown and described, characterized by its relatively large flower clusters containing many closely grouped florets which, when mature, have a solid red-purple coloration, the plant being of bushy form, medium height, and with abundant foliage.

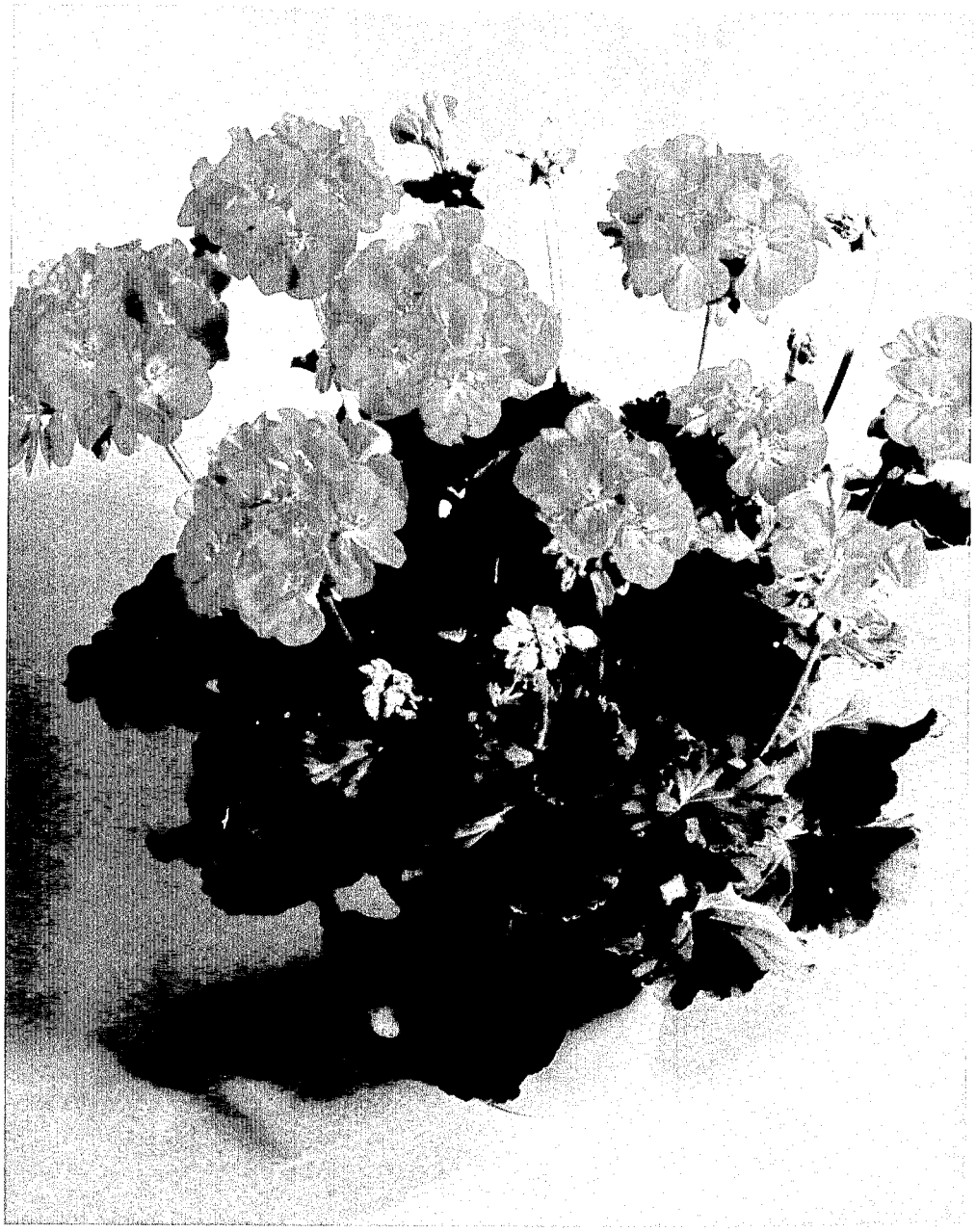

* * * * *